United States Patent [19]

Navas

[11] Patent Number: 5,540,688

[45] Date of Patent: Jul. 30, 1996

[54] INTERVERTEBRAL STABILIZATION DEVICE INCORPORATING DAMPERS

[75] Inventor: Fernand Navas, Charbonnieres Les Bains, France

[73] Assignee: Societe "PSI", Lyons, France

[21] Appl. No.: 207,259

[22] Filed: Mar. 8, 1994

Related U.S. Application Data

[63] Continuation of Ser. No. 888,130, May 26, 1992, abandoned.

[30] Foreign Application Priority Data

May 30, 1991 [FR] France ................... 91 06695

[51] Int. Cl.$^6$ ................... A61F 5/04; A61F 2/44
[52] U.S. Cl. ................... 606/61; A61F/5/04; A61F/2/44; 623/17; 606/72
[58] Field of Search ................... 623/16, 17, 18; 606/61, 75

[56] References Cited

U.S. PATENT DOCUMENTS

| | | | |
|---|---|---|---|
| 3,807,394 | 4/1974 | Attenborough | 606/60 |
| 4,697,582 | 10/1987 | Williams | 606/61 |
| 4,743,260 | 5/1988 | Burton | 623/17 |
| 4,792,339 | 12/1988 | Tepic | 622/23 |
| 4,988,349 | 1/1991 | Pennig | 606/57 |
| 5,002,576 | 3/1991 | Fuhrmann | 623/17 |
| 5,010,879 | 4/1991 | Moriya et al. | 606/61 |
| 5,055,104 | 10/1991 | Ray | 606/61 |
| 5,062,850 | 11/1991 | MacMillan et al. | 606/61 |
| 5,071,437 | 12/1991 | Steffee | 606/61 |
| 5,092,866 | 3/1992 | Breard et al. | 606/57 |
| 5,129,388 | 7/1992 | Vignaud et al. | 606/61 |
| 5,171,278 | 12/1992 | Pisharodi | 606/61 |
| 5,180,393 | 1/1993 | Commarmond | 606/61 |

FOREIGN PATENT DOCUMENTS

| | | | |
|---|---|---|---|
| 0322334 | 6/1989 | European Pat. Off. | 606/61 |
| 2636227 | 9/1988 | France | 606/61 |
| 0848009 | 7/1981 | U.S.S.R. | 606/61 |
| 0897232 | 1/1982 | U.S.S.R. | 606/57 |
| 1136803 | 1/1985 | U.S.S.R. | 606/61 |

*Primary Examiner*—David J. Isabella
*Attorney, Agent, or Firm*—Dowell & Dowell

[57] ABSTRACT

An intervertebral stabilization device is disclosed, made in the form of a damper adapted to resist elastically, on the one hand, an elongation and, on the other hand, an axial compression without buckling, as well as of at least two implants anchored on two adjacent vertebrae.

20 Claims, 6 Drawing Sheets

INTERVERTEBRAL STABILIZATION DEVICE INCORPORATING DAMPERS

This application is a continuation of application Ser. No. 07/888,130, filed May 26, 1992, now abondoned.

BACKGROUND OF THE INVENTION

The present invention relates to intervertebral stabilization devices intended for maintaining at least two vertebrae, whose common disc is worn, in suitable relative position.

It is known that, in the course of ageing, the intervertebral discs risk wearing, with the result that the movements of the intervertebral articulation change, becoming abnormally more ample. The vertebrae may then move in excessive manner with respect to one another, causing permanent displacements as the vertebrae are badly positioned.

The intervertebral disc behaves more like a distributor of pressure or a three-dimensional coupler of movements than as a simple absorber of longitudinal loads.

The intervertebral movement is guided by the set of posterior articulations. The latter have only one degree of freedom; the two surfaces being able only to slide on each other.

During this movement, the disc deforms elastically, progressively braking the movement and dampening it completely at the end of amplitude.

The disc presents a visco-elastic quality. It progressively adapts by viscosity to a new anatomical relation. Consequently, the return movement is then taken over by a similar progressive damper, and this rapidly from its origin.

The set of the articular facets may be asymmetrical and consequently may create a three-dimensional movement coupling lateral bending and horizontal rotation.

This complex movement is itself coupled to the large movement of bending-extension. In complete bending as in complete extension, the amplitude of the combined movement (bending-rotation) becomes zero while it obtains a maximum amplitude in anatomical position, i.e. in the natural anatomical relation of the vertebrae when one is standing or when one is walking (in fact, in an intermediate position between bending and maximum extension).

The biological degradation of the disc disturbs these mechanics of coupled and dampened movements.

This evolution is a source of discomfort and of pain.

U.S. Pat. No. 4 743 260, for example, already proposes placing between at least two adjacent vertebrae a flexible stabilization device composed of two elements fixed to the vertebrae in question. The stabilization elements are made of a non-metallic material which is resistant but sufficiently flexible to allow at least a normal movement of the backbone.

The stabilization elements in question are made of a carbon-fiber-reinforced plastic material, with the result that they have a certain flexibility. However, this flexibility is limited to very small amplitudes in the sense of their curvatures, but no elasticity in traction or in compression.

It has thus been proposed to place a supple, non-elastic tie between two vertebrae to limit like a sudden brake, the movement in its amplitude in bending. At that stage, it behaves like a rigid system, transferring the mechanical stresses on the adjacent intervertebral articulations.

This comes back to the complications of mechanical overload as for arthrodeses or rigid metal assemblies.

Furthermore, the degenerative pathological movement between two vertebrae is not only a movement of exaggerated amplitude but also a subtle disorganzation of the three-dimensional coupling of different degrees of freedom.

A simple supple tie can but help, only insofar as it positions the two vertebrae in an extreme amplitude and therefore in extension.

The residual micro-movements possible due to the creeping of the tie are capable of contributing an elementary, rough adaptation with respect to functional needs. However, their existence clearly differentiates this fixation with respect to the rigid system (arthrodesis or metallic fixation).

It is an object of the improvements forming the subject matter of the present invention to produce devices capable of accompanying the ageing of the discs and which therefore constitute prostheses avoiding the drawbacks mentioned hereinabove.

It will be understood that the purpose of the proposed system is to make good in the most physiologically possible the shortcomings of the disc created by the biological and pathological conditions.

The system proposed aims at obtaining a new stability from an intervertebral position approaching the neutral position (between bending-extension).

In this position, the possibility of movements of the posterior articular surfaces is greater in particular in the sense of extension.

Furthermore, the asymmetrical work of the two posterior surfaces is possible.

The stability of the intervertebral articulation is then obtained due to the quality of damper of the device according to the invention.

The role of the invention is to accompany the movement of the articulation by limiting it slightly in bending and by avoiding abnormal displacements. Operating in parallel, while maintaining the vertebrae in extension with respect to one another, the invention avoids too much contact of the articular surfaces on one another. The system according to the invention also limits the closure of the lateral recess, consequently preventing the possible compression of the nerve root.

SUMMARY OF THE INVENTION

To that end, the invention comprises a damper adapted elastically to resist, elongation and axial compression. The damper is associated with at least two implants anchored on two adjacent vertebrae.

The damper is in the form of an elongated body provided with a bulged or enlarged central part joined by two necks to two enlarged ends cooperating with the implants.

In this way, the damper according to the invention may exert a distracting or compressive force, which enables it to act permanently on the poor intervertebral position.

In other words, the stabilization device according to the invention guides and limits the movement of the intervertebral articulation, while being capable of exerting permanent forces modifying the position of the vertebrae with respect to one another.

The stabilization device according to the invention is capable of damping the movement in bending and in extension and, consequently, of allowing asymmetrical work of the surfaces of the vertebrae while allowing the resultant three-dimensional coupled movement.

In this way, one approaches a complex and damped physiological movement.

Of course, one single device according to the invention, or several, may be used to join two adjacent vertebrae.

BRIEF DESCRIPTION OF THE DRAWINGS

The invention will be more readily understood on reading the following description with reference to the accompanying drawings, in which.

DETAILED DESCRIPTION OF THE DRAWINGS

Figure 1:
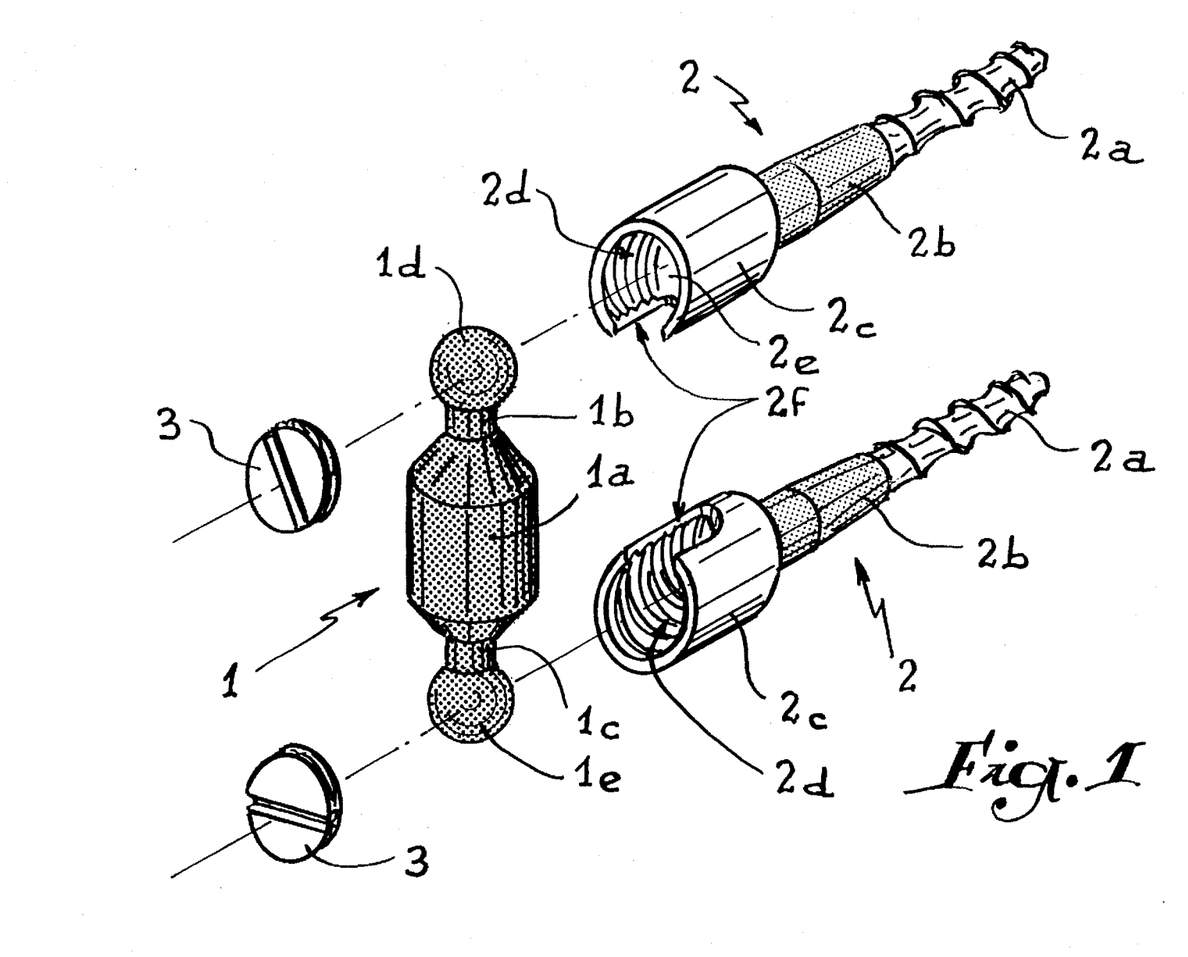
FIG. 1 is a view in perspective of the different elements constituting a stabilization device according to the invention.

Referring now to the drawings, and firstly to FIG. 1, the device according to the invention essentially comprises a damper 1 made of a bio-compatible, elastic material and two implants 2 screwed in two adjacent vertebrae and whose free ends are associated with the two ends of the damper 1.

It is observed that the damper 1 is made in the form of an elongated body provided with a bulged or enlarged central part 1a joined to two necks 1b, 1c to two bulbous ends 1d, 1e. In am advantageous embodiment of the preceding arrangement, the bulged part 1a may be provided to be of elliptic longitudinal section, while the two ends 1d and 1c each take the form of a sphere. Of course, the part 1a may be of cylindrical section with two truncated endpieces or in the form of two frustums of cone or may be asymmetrical in particular applications.

Figure 2:
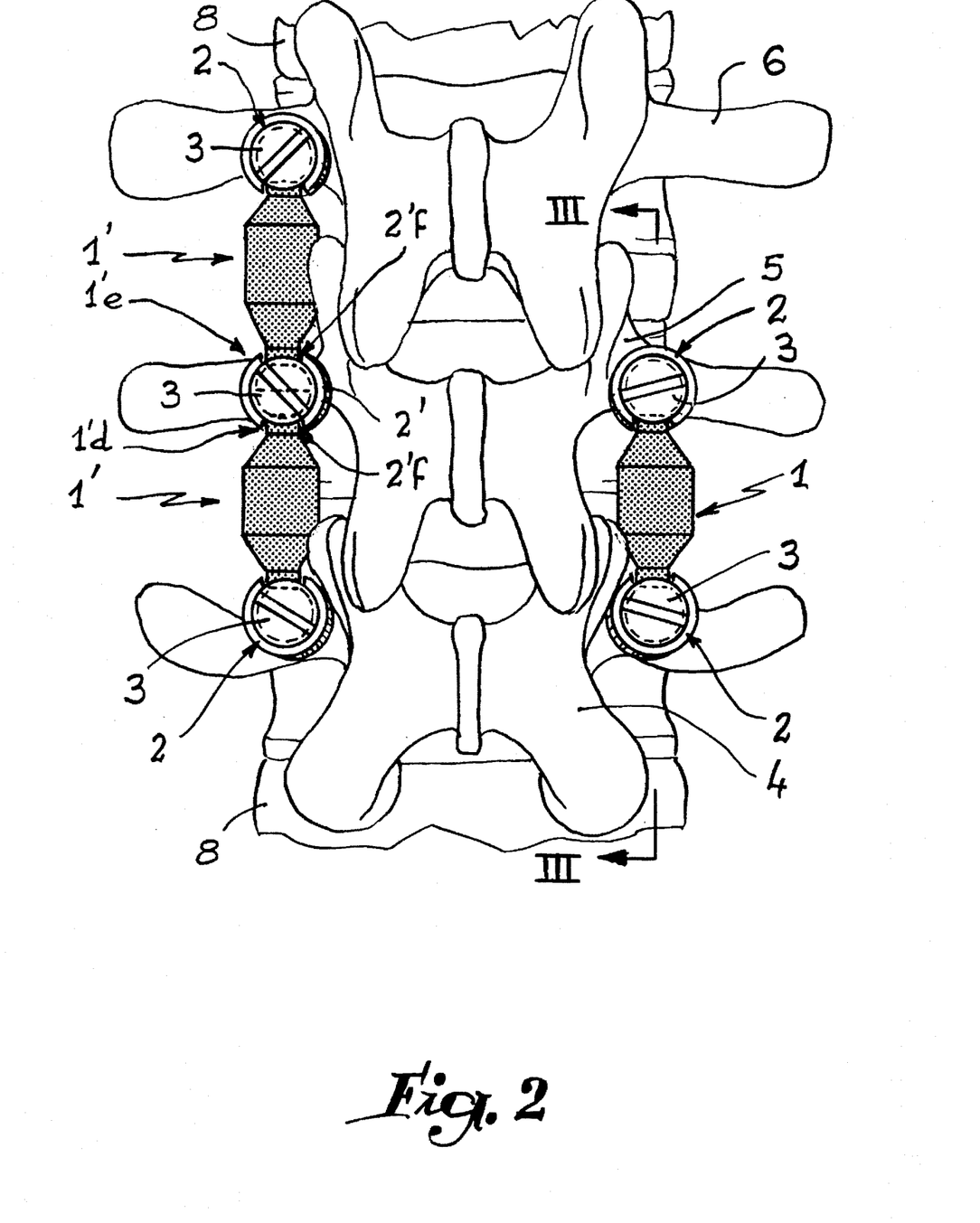
FIG. 2 is a view from behind of three vertebrae associated with the stabilization devices according to the invention.
Figure 3:
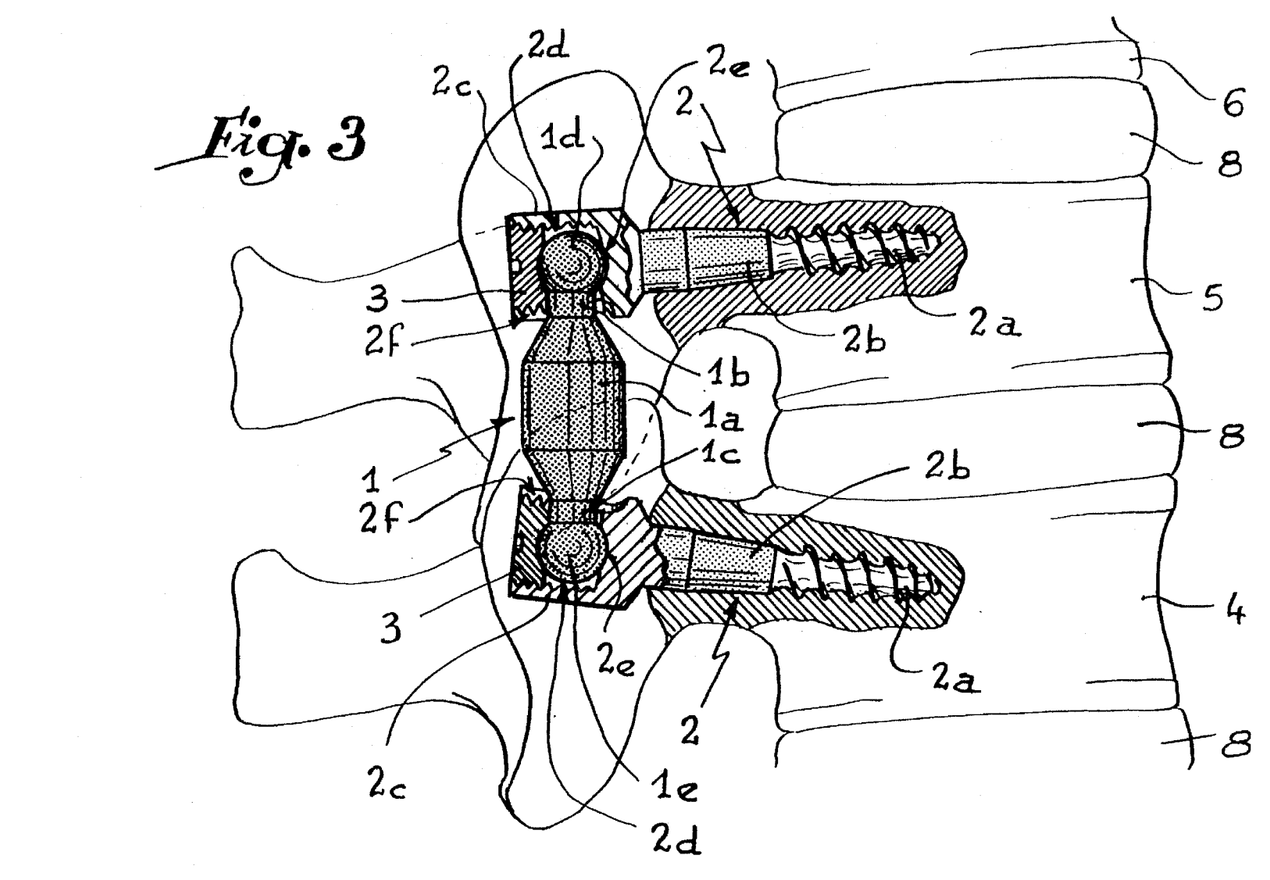
FIG. 3 is a section along III—III (FIG. 2).

Each implant 1 includes a screw 2a adapted to be screwed in the pedicle of a vertebra or in any other location thereof. The screw 2a extends from a cylindrical body 2b which terminates in a hollow socket or receptical 2c of cylindrical shape with a tapped inner wall 2d and a concave bottom 2e presenting a shape complementary to that of half the end 1d, 1e of the damper. It is observed that the socket 2c is provided with a lateral notch 2f adapted to allow passage of the neck 1b, 1c of the damper 1 for positioning the damper with respect to the implants. Locking of the ends of the damper 1 is effected after they have been placed in the sockets 2c by screwing a threaded endpiece 3 inside the corresponding socket with respect to the tapped wall 2d. Of course, the base 3a of the endpiece 3 is provided to be concave and hemispherical, so as to cooperate exactly with the spherical ends 1d, 1e of the damper. FIGS. 2 and 3 illustrate the assembly of a device according to the invention with respect to two adjacent vertebrae 4 and 5 of a spine.

On the right-hand side of FIG. 2, a device has been illustrated, comprising one damper 1 associated with two implants 2 each fastened to a vertebra 4, 5. The same assembly may be provided in the left-hand part. In addition, it is possible that three successive vertebrae 4, 5, 6 need stabilization. In that case, one of the implants 2' comprises two diametrally opposite notches 2'f, while the ends of the two dampers 1' each comprise one end 1'd, 1'e, truncated along a diametral plane of the sphere perpendicular to the longitudinal axis of the damper in order that the two truncated ends 1'd, 1'e may be retained in the socket of the implant 2' (cf. the left-hand part of FIG. 2).

FIG. 3 shows in very detailed manner the structure of the assembly of the ends of the damper with two implants. The hollow socket 2c with bellied concave base 2e is found again, as well as the endpiece 3 with bellied concave base 3a in order that the two spherical ends 1c, 1d of the damper 1 are suitably locked with respect to the implants 2. Such locking makes it possible to create a sort of ball-joint articulation facilitating the movements of the spine.

Figure 4:
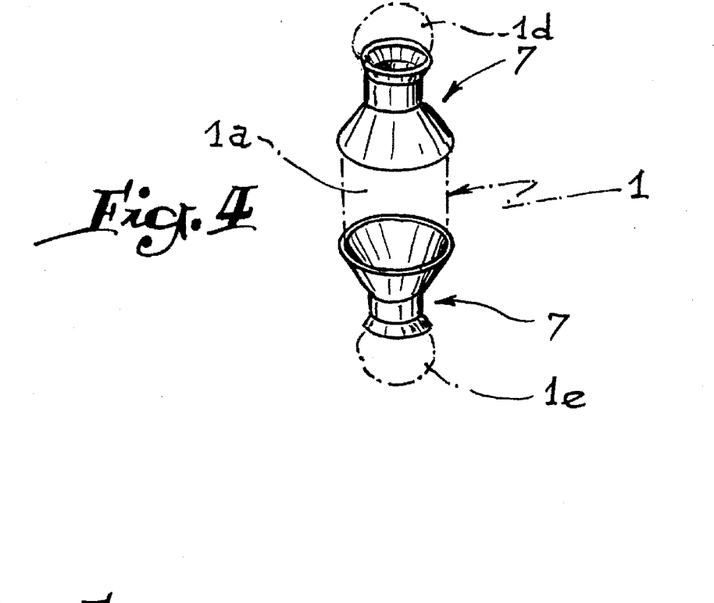
FIG. 4 is a view in perspective of two bushes adapted to cooperate with the necks of the damper of a device according to the invention.

As illustrated in FIG. 4, the necks 1b, 1c of the damper 1 are advantageously protected by a bush 7 made of metal or any other rigid material and which ensures the mechanical quality of the relation between the damper and the implants. The bushes 7 may comprise on their inner faces notches which intervene actively, reducing mechanical efforts in the corresponding neck.

As illustrated in FIGS. 2 and 3, the stabilization device according to the invention is positioned either on the posterior face or on the lateral face of the vertebrae. It may also be used at the front of the vertebral body, as illustrated in FIG. 5.

Figure 5:
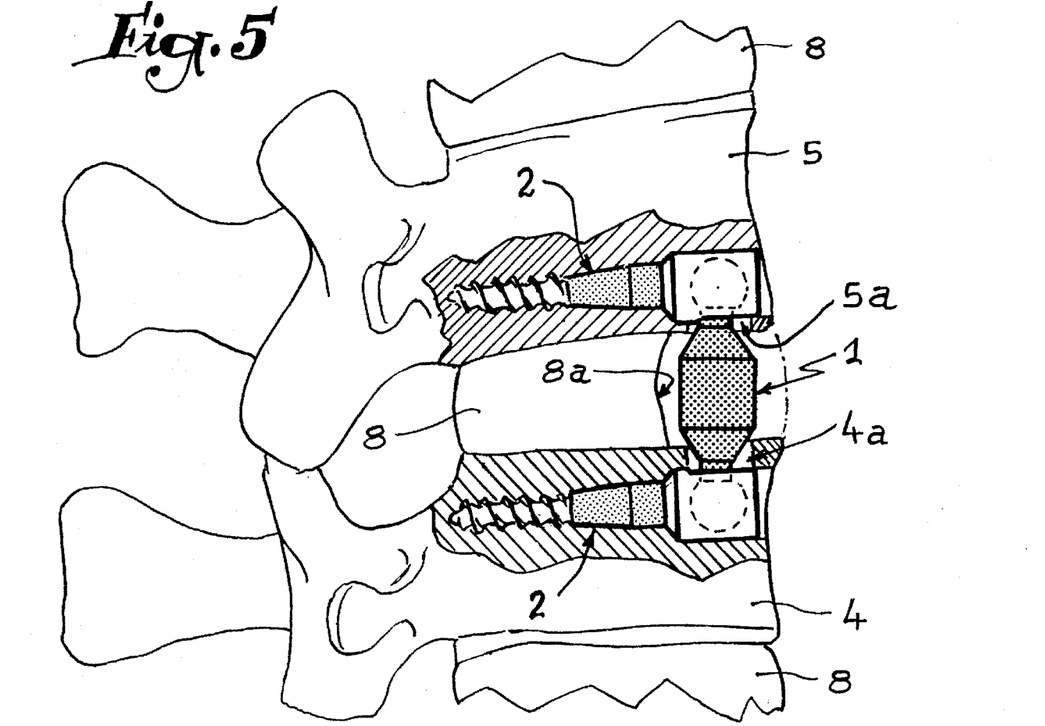
FIG. 5 is a view similar to that of FIG. 3, but illustrating the assembly of a device according to the invention in anterior position.

In this mode of positioning, it goes without saying that the implants 2 must be disposed laterally outside the vessels or the device will be placed as illustrated in FIG. 5, i.e. embedded in the vertebra.

In that case, a slight resection of the intervertebral disc 8 is made to form a depression 8a therein. The implants 2 are driven deeply in the vertebra so that their socket 2c is embedded in the vertebra which is itself notched at 4a, 5a in order to allow passage of the two necks of the damper. It is thus ensured that the device does not interfere with the vessels located along the anterior face of the spine.

The dampers may be provided with different lengths varying from some millimeters with respect to one another so that the length of the damper can be adjusted to the anatomical pathology of the patient.

A stabilization system has thus been produced, making it possible to obtain a set of the residual intervertebral movements necessary for the elementary physiology of the spine, while eliminating the bad positions of the vertebrae and abnormal movements thereof.

Any appropriate material may be used for making the damper 1, in particular a bio-compatible elastomer. A composite material may also be adopted, optimally responding to the two mechanical requirements of the damper, viz. the resistance to longitudinal traction and to a compression without buckling. The materials chosen may be of the same family or totally different.

Figure 6:
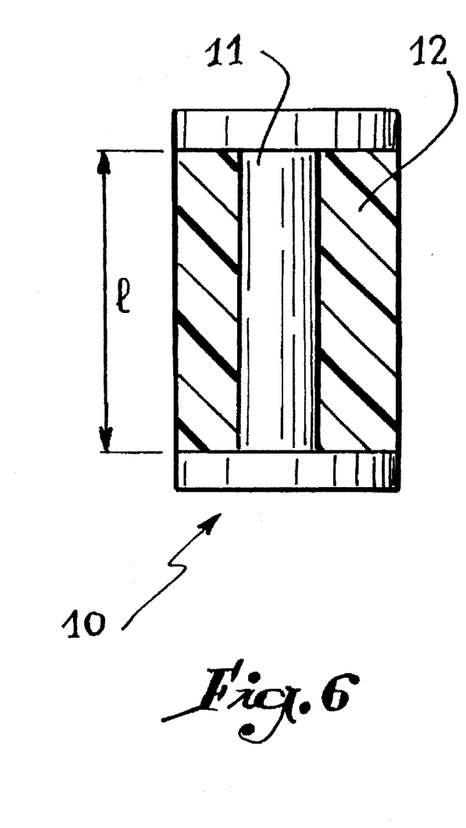
FIG. 6 is a very schematic view in section of the principle of a damper in accordance with a variant embodiment of the invention.
Figure 7:
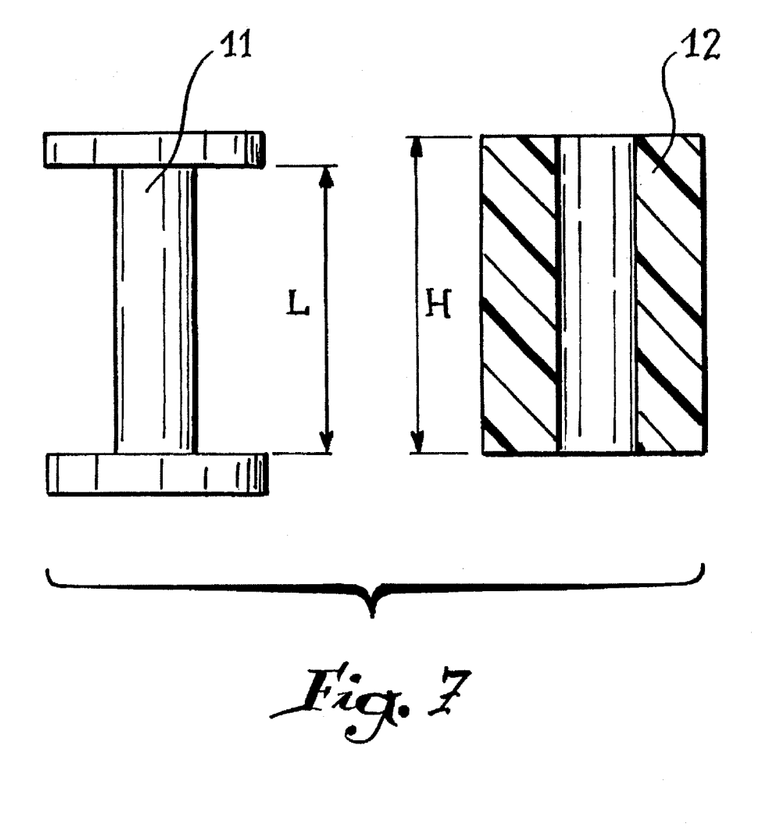
FIG. 7 shows in section, in the free state, the two elements of the damper of FIG. 1.

The principle of the damper made of a composite material is illustrated in FIGS. 6 and 7. The damper, referenced 10, comprises two elements 11 and 12 both made of bio-compatible elastic materials. The first element 11 is in the form of a spool of which the distance between the flanges is referenced L in the free state. The second element, referenced 12, takes the form of a tubular sleeve of height H in the free state. Assembly of the damper consists in placing element 12 between the flanges of the element 11 after the latter has been elongated. Therefore, the element 11 compresses by its flanges the element 12 in the sense of compression, while the latter maintains element 11 in a pre-tensioned position. In this way, the length 1 of the sleeve after assembly and which corresponds to the distance between the flanges of element 12 is defined by the relation L<1<H.

Figure 8:
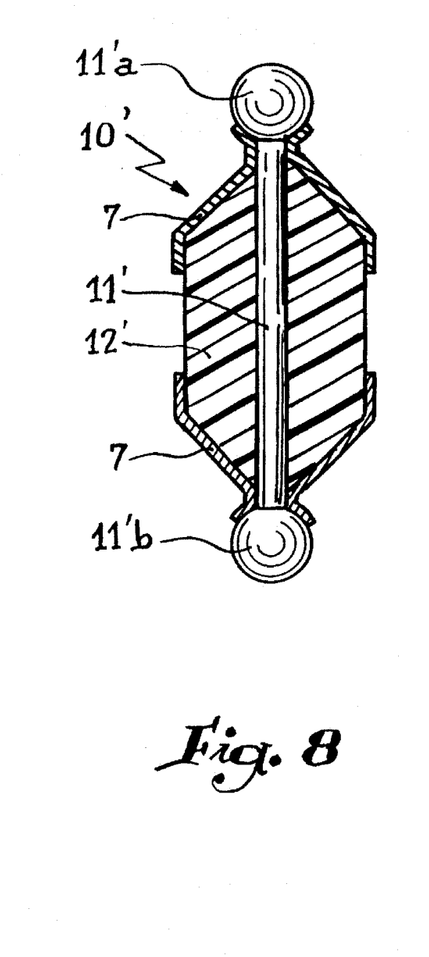
FIGS. 8, 9 and 10 are longitudinal sections of three different embodiments of the damper illustrated in FIG. 6.

In a first practical embodiment illustrated in FIG. 8, element 11' or core takes the form of dumb-bells, while element 12 is made in the form of a body 12' whose general shape is that of the centre of the damper 1 of FIGS. 1, 2 and 3.

In order to produce such a damper, the core 11' is made. The rod thereof is elongated elastically in the axial sense, then the body 12' is moulded on this core. After manufacture, the core 11'a is pre-tensioned, while the body 12' is pre-compressed. It will be noted that the core 11' and the body 12' are joined by means of two bushes 7 in the form of diabolos, the ends of the core 11' projecting beyond the ends; of the body 12', while the two spherical heads 11'a, 11'b of the core correspond to the spheres 1d, 1e of the damper 1.

Figure 9:
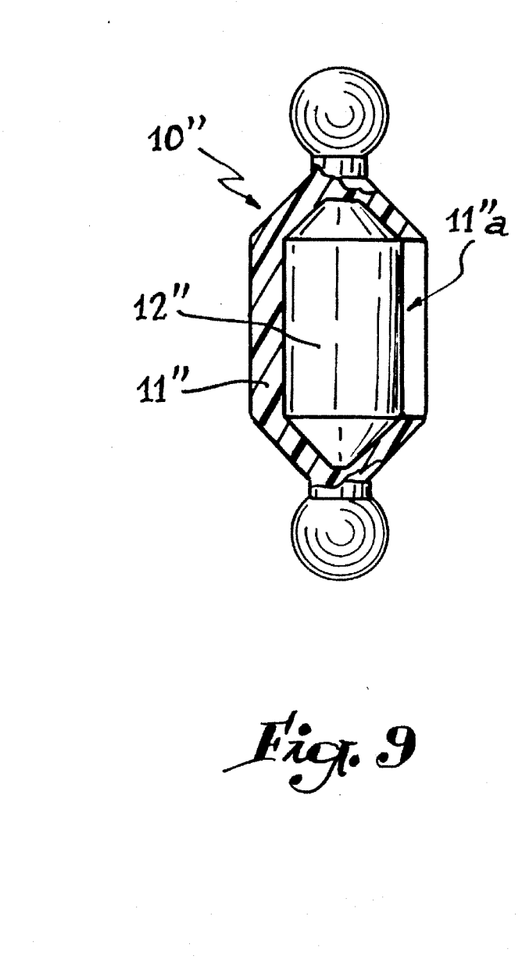

In a second embodiment illustrated in FIG. 9, the damper referenced 10", comprises an elastic envelope 11" of which the outer shape corresponds to that of the damper 1, as well as a block of elastic material. 12". After manufacture, the envelope 11" which comprises a hollow inner cavity, is elongated so as to increase the height of its cavity in which the block 12" is introduced via a lateral opening 11"a or the like. The envelope 11" is consequently pre-tensioned in elongation, while the block 12" is pre-compressed by the action of the envelope.

Figure 10:
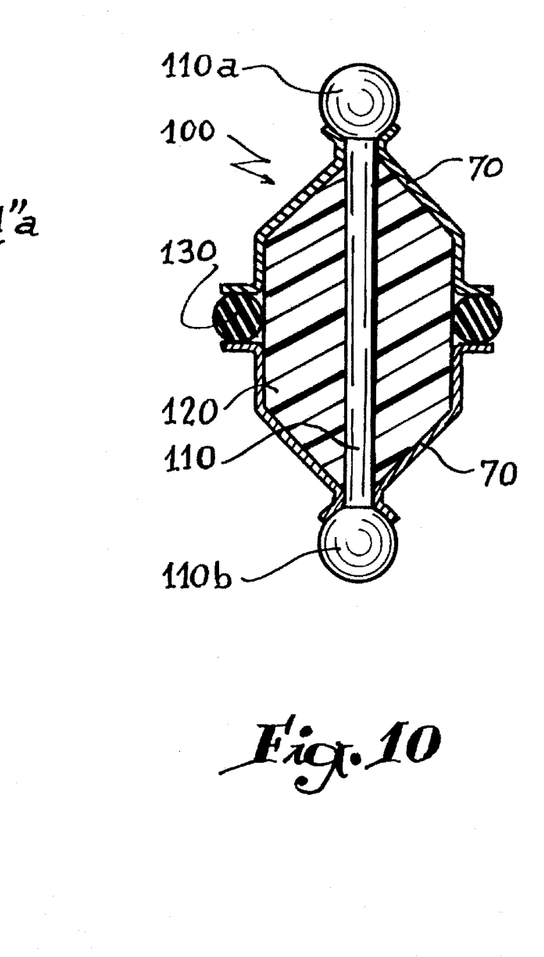

Finally, in a practical embodiment illustrated in FIG. 10, the damper 100 comprises a body 120 which is mounted on an element 110 in the form of dumb-bells as already shown in FIG. 8. The element 110 and the body 120 are joined by means of two sleeves 70 in the form of diabolos of which one of their ends abuts against the spherical heads 110a and 110b of the element 110 corresponding to the spheres 1d, 1e of the damper 1. The other ends of the sleeves 70 are respectively curved towards the outside of the damper 100 in order to form a circular free space inside which is introduced an O-ring 130. This latter makes it possible to compensate the efforts of compression of the damper 100.

It is ascertained that the O-ring 130 may be made of a bio-compatible material similar to that of the body 12 so as to be able to resist the efforts of compression. The O-ring 30 and the dumb-bell shaped element 110 may be used together on the same damper or independently of each other depending on the stresses to be regulated.

The hardness of the elements composing the damper 10', 10" will be chosen so that, under the effect of the forces applied by the vertebrae, none of the elements resumes its dimensions in the free state.

In this way, whether the damper is subjected to a force of traction or to a force of compression, it still remains pre-stressed, so that the force which is applied thereto is always damped at some point within the amplitude of the movement imposed on the composite damper.

It must, moreover, be understood that the foregoing description has been given only by way of example and that it in no way limits the domain of the invention which would not be exceeded by replacing the details of execution described by any other equivalents.

What is claimed is:

1. An intervertebral stabilization device to stabilize the movement between at least two vertebrae of a patient's spine which are positioned on opposite sides of a spinal disc, said device comprising, two anchoring elements each having means to be anchored to adjacent (vertebrate) vertebrae and a free end, a dampening element for dampening elongation of the spine during either axial tension or compression thereof, and said dampening element configured to extend generally exteriorly of the spinal disc and between said free ends of said anchoring elements, said dampening element including opposite ends, and locking means for securing said opposite ends to said free ends of said anchoring elements so that said dampening element works against said free ends to dampen elongation of the spine during either axial tension or compression of the spine.

2. The device of claim 1, wherein said dampening element has an elongated body, said body having an enlarged central portion and said opposite (enlarged) ends being enlarged, and a reduced neck portion joining each of said enlarged ends to opposite ends of said central portion.

3. An intervertebral stabilization device for stabilizing the movement between at least two vertebrae which are positioned on opposite sides of a spinal disc, said device comprising: two anchoring elements each having means to be anchored to adjacent vertebrae, a dampening element configured to be positioned and extending between and connected to said anchoring elements, said dampening element having an elongated body, said body having a central portion and opposite enlarged ends, each anchoring element including a socket means at one end thereof for receiving one of said enlarged ends, each of said socket means having a concave bottom surface shaped for close cooperation with said enlarged ends, securing means for retaining said enlarged ends, within said socket means, and said dampening element capable of resisting elastic elongation during either axial tension or compression of the spine.

4. The device of claim 3, wherein said socket means includes a tapped hole and a notch which opens laterally thereof, and said securing means includes a threaded end piece having a hemispherical base, said end piece being threadingly received within said tapped hole.

5. The device of claim 4, wherein said socket means includes two generally opposing notches therein, and at least one of the enlarged ends of said dampening element is hemispherical in configuration.

6. The device of claim 4, including a reduced neck portion between each of said enlarged ends and said central position, and a rigid sleeve means surrounding each of said reduced neck portions of said dampening element.

7. The device of claim 6, wherein the dampening element is made of a bio-compatible elastomer.

8. The device of claim 6, wherein the dampening element is made of two material components.

9. The device of claim 6, wherein said central portion of said elongated body has an elliptical shape in longitudinal cross-section.

10. The device of claim 6, wherein said central portion of said elongated body is asymmetrical.

11. The device of claim 8, wherein a first of said material components is pre-stressed in extension and the other of said material components is pre-stressed in compression.

12. The device of claim 11, wherein said first material component is in the form of a dumb-bell having a central rod portion and outer enlarged portions and said other material component is in the form of a sleeve which surrounds said rod portion and which sleeve is placed in compression by said outer enlarged portions.

13. The device of claim 11, in which said first material portion is in the form of an elastic envelope defining a cavity therein and said other material component is in the form of a block of elastic material placed in compression within said envelope.

14. The device of claim 11, in which said first material component includes a central element, said second material component being in the form of a sleeve surrounding said central element, a pair of opposing sleeve means surrounding said sleeve and extending inwardly toward one another and forming an annular space therebetween, and an O-ring means positioned within said annular space.

15. The device of claim 14, wherein the O-ring is made of a bio-compatible material which is resistant to compressive forces.

16. The device of claim 1, wherein the dampening element is made of two material components.

17. The device of claim 16, wherein a first of said material components is pre-stressed in extension and the other of said material components is prestressed in compression.

18. The device of claim 17, wherein said first material component is in the form of a dumb-bell having a central rod portion and outer enlarged portions forming said opposite ends of said dampening element, and said other material component is in the form of a sleeve which surrounds said rod portion and which sleeve is placed in compression by said outer enlarged portions.

19. The device of claim 17, in which said first material portion is in the form of an elastic envelope defining a cavity therein and said other material component is in the form of a block of elastic material placed in compression within said envelope.

20. The device of claim 17, in which said first material component includes a central element, said second material component being in the form of a sleeve surrounding said central element, a pair of opposing sleeve means surrounding said sleeve and extending inwardly toward one another and forming an annular space therebetween, and an O-ring means positioned within said annular space.

* * * * *